United States Patent [19]

Kons et al.

[11] Patent Number: 5,037,418

[45] Date of Patent: Aug. 6, 1991

[54] ABSORBENT ARTICLE HAVING AN ATTACHABLE UNDERGARMENT PROTECTIVE SHEET

[75] Inventors: Hugo L. Kons, Appleton; Susan C. Paul, Neenah, both of Wis.

[73] Assignee: Kimberly-Clark Corporation, Neenah, Wis.

[21] Appl. No.: 427,667

[22] Filed: Oct. 27, 1989

Related U.S. Application Data

[63] Continuation-in-part of Ser. No. 933,828, Nov. 24, 1986, abandoned.

[51] Int. Cl.$^5$ ............................................. A61F 13/10
[52] U.S. Cl. .............................. 604/387; 604/385.1; 604/386; 604/397; 604/390
[58] Field of Search ............ 604/384, 385.1, 385.2, 604/387, 390, 392, 393, 397, 400, 402, 386, 398

[56] References Cited

U.S. PATENT DOCUMENTS

| | | | |
|---|---|---|---|
| 3,397,697 | 8/1968 | Rickard | 128/288 |
| 3,688,771 | 9/1972 | Werner | 604/364 |
| 4,285,343 | 8/1981 | McNair | 128/287 |
| 4,402,689 | 9/1983 | Baum | 604/387 |
| 4,589,876 | 5/1986 | Van Tilburg | 604/385 R |
| 4,605,405 | 8/1986 | Lassen | 604/389 |
| 4,608,047 | 8/1986 | Mattingly | 604/387 |
| 4,615,696 | 10/1986 | Jackson et al. | 604/389 |
| 4,687,478 | 8/1987 | Van Tilburg | 604/387 |
| 4,735,316 | 4/1988 | Fröidh et al. | 206/438 |
| 4,846,828 | 6/1989 | Mendelson | 604/387 |
| 4,857,066 | 8/1989 | Allison | 604/385.1 |
| 4,900,320 | 2/1990 | McCoy | 604/387 |

FOREIGN PATENT DOCUMENTS 2143439 2/1985 United Kingdom .

*Primary Examiner*—C. Fred Rosenbaum
*Assistant Examiner*—Mark O. Polutta
*Attorney, Agent, or Firm*—Thomas J. Connelly

[57] ABSTRACT

An absorbent article is disclosed having an absorbent with a bodyside surface and a garment facing surface. A liquid-impermeable baffle is positioned adjacent to the garment facing surface of the absorbent and a liquid-permeable cover cooperates with the baffle to enclose the absorbent and form a pad. The pad has a pair of longitudinal side edges and a pair of distally spaced ends. A garment adhesive strip is secured to the garment facing surface of the pad and is positioned along the longitudinal axis thereof. The garment adhesive strip provides attachment of the pad to the crotch portion of the undergarment. A pair of adhesive strips are secured to the cover and are positioned on opposite sides of the garment adhesive strip. A liquid-impermeable protective sheet can be optionally attached to the pair of adhesive strips to prevent side leakage of body fluid off of the pad from staining the crotch portion of the undergarment.

18 Claims, 5 Drawing Sheets

ABSORBENT ARTICLE HAVING AN ATTACHABLE UNDERGARMENT PROTECTIVE SHEET

This application is a continuation-in-part of application Ser. No. 933,828, filed Nov. 24, 1986 now abandoned.

FIELD OF THE INVENTION

This invention relates to an absorbent article having an optionally attachable undergarment protective sheet. More particularly, it relates to an sanitary napkin having an optionally attachable liquid-impermeable sheet which can be attached to the longitudinal sides of the sanitary napkin and is sized to surround the crotch portion of an undergarment to prevent the undergarment from being stained by body fluids.

BACKGROUND OF THE INVENTION

Currently, a wide variety of products for absorption of human body fluids are available in the form of feminine pads, sanitary napkins, panty shields, panty liners and incontinence devices. These products generally have an absorbent positioned between a liquid-permeable bodyside cover and a liquid-impermeable garment facing baffle. A pressure-sensitive adhesive which is secured to the baffle is generally used to attach the product to the inner crotch portion of an undergarment.

While such products are widely used, the problem of leakage of body fluid at the sides of the products still remains. Such leakage can stain the undergarment and this is viewed as being unacceptable to the consumer. U.S. Pat. No. 4,605,405 issued to Lassen and assigned to the present assignee, teaches a dynamically moveable sanitary napkin which uses attachment means to position the napkin relative to an undergarment. The sanitary napkin utilizes a retention strap and a positioning strap to keep it in place. However, neither strap adequately can prevent side leakage of body fluids.

U.S. patents which directly relate to controlling side leakage include: 3,397,697; 4,285,343; 4,589,876; 4,608,047 and 4,687,478. These patents teach the use of side flaps which extend laterally outward from the absorbent. The flaps are designed to fold upon themselves or wrap around the undergarment to provide protection. While these devices are successful, some are costly to manufacture as they require complicated shapes creating excessive trim waste. In addition, some are awkward to use and require careful placement within the crotch portion of the undergarment. The folding and attachment of the side flaps can also make release of the product from the undergarment difficult and inconvenient. Still further, many times the wearer has a light flow and does not require the side flaps. In these situations, the wearer would prefer not to use the side flaps and the prior art products do not offer this option. Accordingly, there remains a need for a product that will provide side leakage protection, be low in cost and give the wearer the option of when to utilize the protective sheet.

SUMMARY OF THE INVENTION

Briefly, the present invention relates to an absorbent article designed to be attached to the crotch portion of an undergarment. The article includes an absorbent having a bodyside surface and an opposite garment facing surface. A liquid-impermeable baffle is positioned adjacent to at least the garment facing surface of the absorbent and a liquid-permeable cover is positioned adjacent to at least the bodyside surface of the absorbent. The cover and baffle cooperate to enclose the absorbent and form a pad having a pair of longitudinal side edges and a pair of distally spaced ends. A garment adhesive strip is secured to the garment facing surface of the pad and is positioned along the longitudinal axis thereof. A pair of adhesive strips are secured to the pad and positioned on opposite sides of the garment adhesive strip. The pair of adhesive strips provide a means of attaching an optionally attachable protective sheet. The protective sheet has a length approximately equal to the length of one of the pair of adhesive strips and a width corresponding to about twice the width of the crotch portion of the undergarment. The protective sheet prevents side leakage of body fluid off of the pad from staining the crotch portion of the undergarment.

The general object of this invention is to provide an absorbent article having an optionally attachable protective sheet to prevent side leakage of body fluids from the absorbent pad to the adjacent undergarment. Another object of this invention is to provide a sanitary napkin with an optionally attachable protective sheet which can be used only when needed, for example on days of heavy menstrual flow.

Still, another object of this invention is to provide a low cost absorbent article with an optionally attachable protective sheet.

A further object of this invention is to provide an absorbent article with an optionally attachable protective sheet which is easy to position relative to an undergarment.

Other objects and advantages of the present invention will become more apparent to those skilled in the art in view of the following description and the accompanying drawings.

DETAILED DESCRIPTION OF THE PREFERRED EMBODIMENTS

Figure 1:
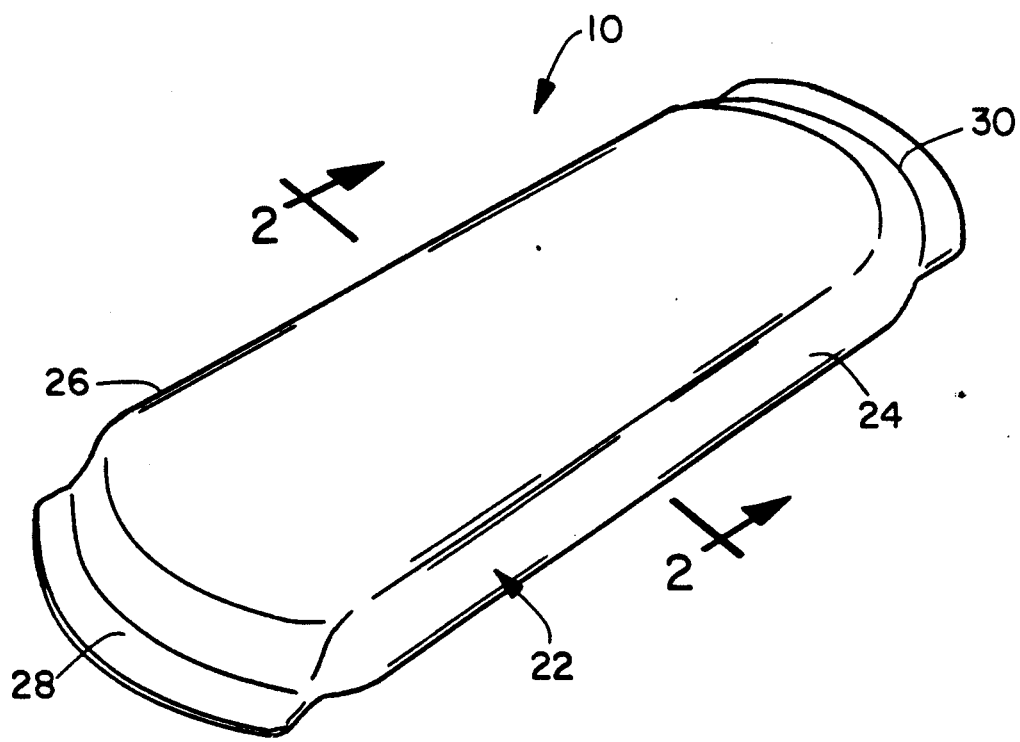
FIG. 1 is a perspective view of an absorbent article in accordance with the invention.
Figure 2:
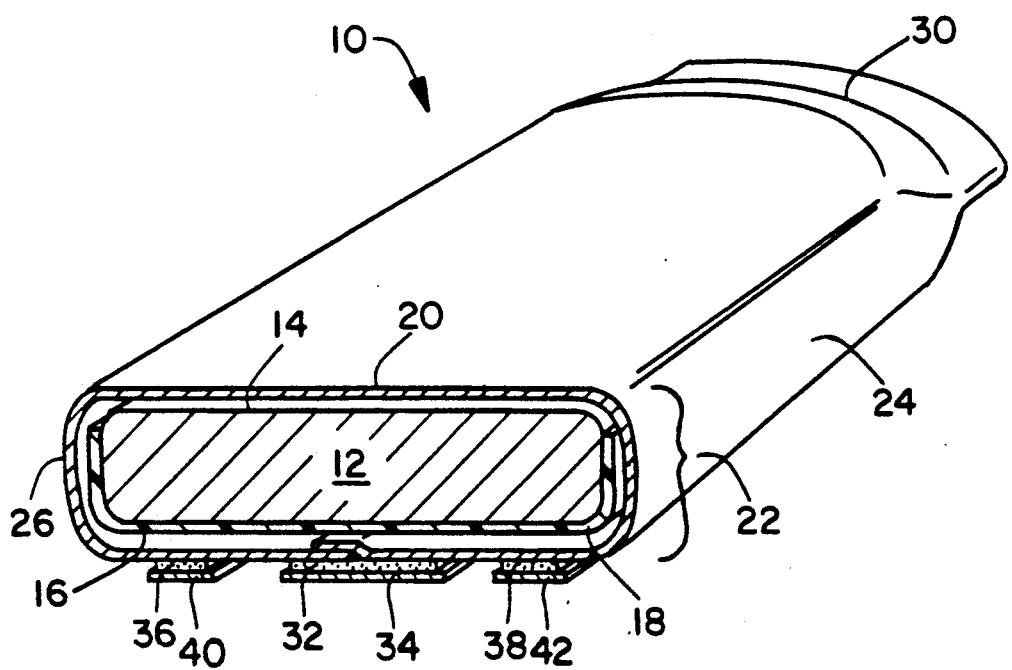
FIG. 2 is a cross-sectional view of the absorbent article shown in FIG. 1 taken along line 2—2.

Referring to FIGS. 1 and 2, an absorbent article 10 is shown for absorbing human exudate. The absorbent article 10, which can be a feminine pad, a sanitary napkin, a panty shield, a panty liner or an incontinence device, includes an absorbent 12 having a bodyside surface 14 and a garment facing surface 16. The absorbent 12 can be made from wood fluff, absorbent polymer filaments such as polypropylene, or a combination of polymer filaments and devilicated wood fibers, polyester or rayon fibers. A liquid-impermeable baffle 18 is positioned adjacent to at least the garment facing surface 16 of the absorbent 12. Preferably, the baffle 18 is made from a polymer material and will extend upward to cover a portion of the sides of the absorbent 12. A liquid-permeable cover 20 is positioned adjacent to at least the bodyside surface 14 of the absorbent 12 and cooperates with the baffle 18 to enclose the absorbent 12. The cover 20 can be made of a liquid-permeable material such as tissue, perforated film or netting. A preferred material is spunbonded polypropylene for it is low in cost and provides good liquid penetration while providing a dry feel to a person's skin.

In FIG. 2., the cover 20 completely surrounds both the absorbent 12 and the baffle 18. However, as shown in some of the other drawings, the cover and the baffle can be sealed together to enclose the absorbent 12.

The absorbent 12, the baffle 18 and the cover 20 form a pad 22 having a pair of longitudinal side edges 24 and 26 and a pair of distally spaced ends 28 and 30.

Figure 3:
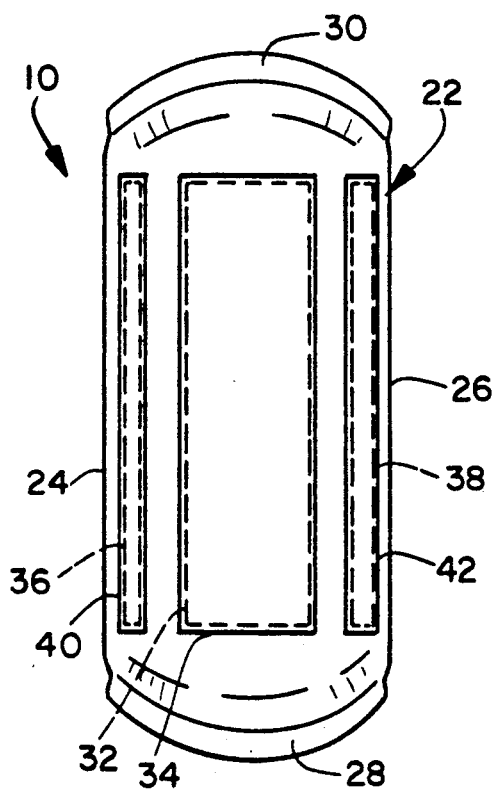
FIG. 3 is a bottom view of the absorbent article depicted in FIG. 1 showing a garment adhesive strip and a pair of adjacent adhesive strips.

Referring to FIG. 3, the absorbent article 10 has a garment adhesive strip 32 secured to the garment facing surface. The adhesive strip 32 can be a single strip of adhesive, a plurality of adhesive lines or a plurality of adhesive dots aligned in a predetermined fashion. The adhesive strip 32 is positioned along the longitudinal axis of the pad 22 and is designed to be covered by a removable or releasable peel strip 34. When a person is ready to use the product, the peel strip 34 is removed and the exposed garment adhesive strip 32 is attached to an inner surface of the crotch portion of an undergarment so as to hold the pad 22 firmly in place. In addition, a pair of adhesive strips 36 and 38 are also secured to the pad 22 and are positioned on opposite sides of the garment adhesive strip 32. The pair of adhesive strips 36 and 38 can have a length less than, equal to or greater than the length of the garment adhesive strip 32. Preferably, the length of the pair of adhesive strips will be about equal to the length of the garment adhesive strip 32. The pair of adhesive strips 36 and 38 are also covered by removable peel strips 40 and 42, respectfully.

Figures 4, 5, 6, 7:
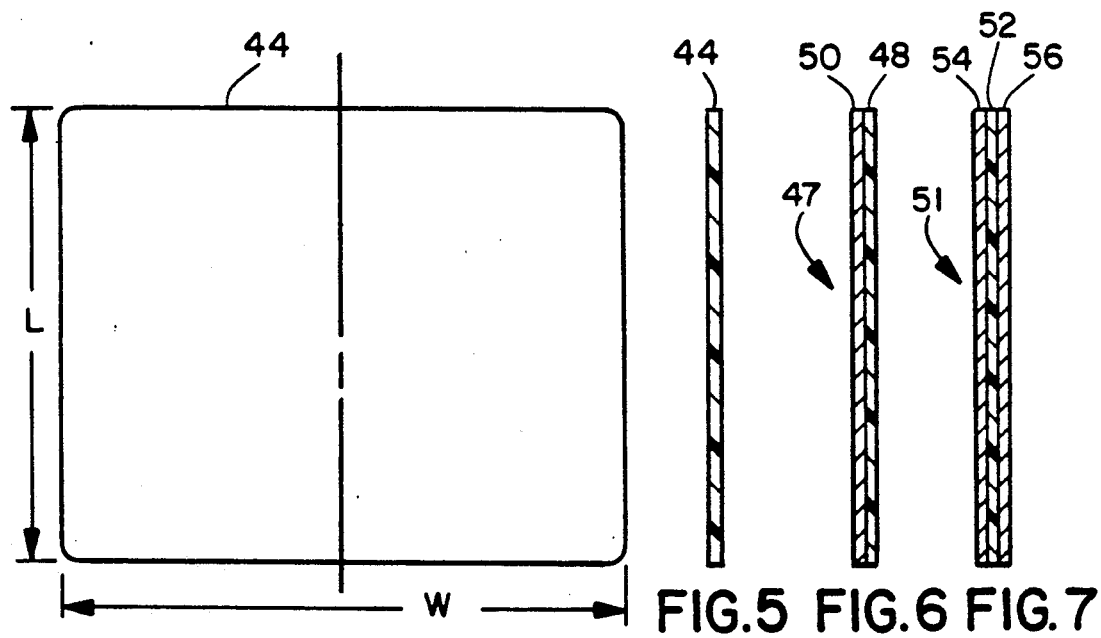
FIG. 4 is a top view of a protective sheet which can be optionally attached to the absorbent article.
FIG. 5 is a side view of the protective sheet depicted in FIG. 4 showing a single liquid-impermeable layer.
FIG. 6 is a side view of an alternative protective sheet formed as a two layer laminate with one layer being liquid-impermeable and the other layer having a cloth-like texture.
FIG. 7 is a side view of still another embodiment of a protective sheet formed as a three layer laminate with the middle layer being liquid-impermeable.

Referring to FIGS. 4 and 5, a protective sheet 44 having a generally rectangular shape is shown which is optionally attachable to the absorbent article 10 via the pair of adhesive strips 36 and 38. The protective sheet 44 is liquid-impermeable and can be made from a polymer film such as polypropylene or polyethylene. The protective sheet 44 has a length approximately equal to the length of one of the pair of adhesive strips 36 and 38, although it could be as long as the pad to which it is designed to be attached. A length of about 5 inches is sufficient and corresponds to the narrow crotch portion of a typical undergarment 46. The sheet 44 should have a width corresponding to at least twice the width of the crotch portion of the typical undergarment 46. Preferably, the width of the protective sheet 44 is about 2 to 2.5 times the width of the crotch portion of the undergarment 46. The protective sheet 44, when attached to the adhesive strips 36 and 38 will prevent side leakage of body fluid off of the pad 22 from staining or soiling the crotch portion of the undergarment 46.

Referring to FIGS. 6 and 7, the protective sheet can be constructed as a laminate having at least one liquid-impermeable layer and at least one layer having a cloth-like texture or feel so as to provide a soft feel against the wearer's legs. In FIG. 6, a two layer protective sheet 47 is shown having a liquid-impermeable layer 48 and a cloth-like layer 50. The cloth-like layer 50 can be made of spunbonded material, cotton, rayon, or other type of woven or non-woven, natural or synthetic material. The cloth-like layer 50 will be positioned away from the undergarment 46 so as to contact the inner thighs of the user. In FIG. 7, a protective sheet 51 is shown as a three layer laminate having a liquid-impermeable layer 52 sandwiched between two outer layers 54 and 56. One or both of the outer layers 54 and 56 can have a cloth-like texture or feel so as to provide a soft and non-abrasive surface against the inner thighs of the wearer.

Figure 8:
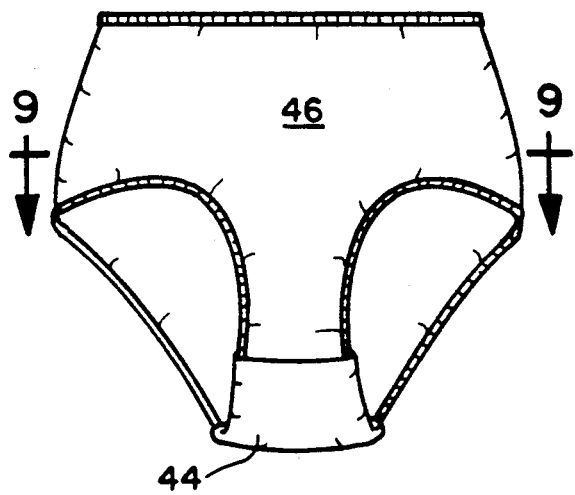
FIG. 8 is a front view of an undergarment having the absorbent article secured to an inner surface thereof and having the optionally attachable protective sheet positioned about the crotch portion thereof.
Figure 9:
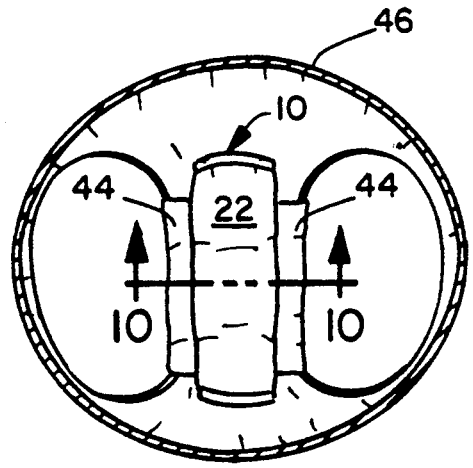
FIG. 9 is a cross-sectional view of the undergarment depicted in FIG. 8 taken along line 9—9 showing the absorbent article secured to an inner surface thereof.
Figure 10:
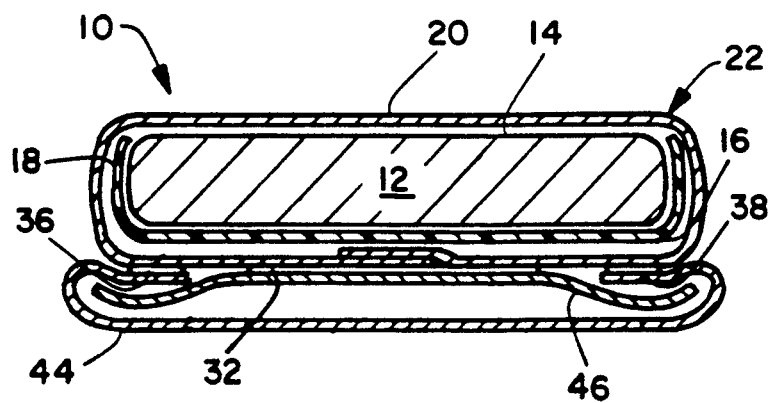
FIG. 10 is a cross-sectional view of the undergarment, absorbent article and the protective sheet shown in FIG. 9 taken along line 10—10.

As illustrated in FIGS. 8–10, the absorbent article 10 is positioned in the crotch portion of the undergarment 46 and is held secure by the garment adhesive strip 32. The peel strips 40 and 42 are removed and one side of the protective sheet 44 is attached or fastened to one of the adhesive strips, for example, strip 36. The protective sheet 44 is then wrapped around the exterior of the crotch portion of the undergarment 46 and its opposite side is attached to the other adhesive strip 38. FIG. 10 best shows the absorbent article 10 with the protective sheet 44 attached in place. The consumer has the option of attaching the protective sheet 44 or of leaving it off depending on personal preferences. If a woman is menstruating, she may attach the protective sheet 44 to give her the extra assurance that her undergarment will not get stained. However, at other times., she may wish to forego the use of the protective sheet 44 because she knows that her bodily discharges will be light and the likelihood of leakage is minimal.

Figure 11:
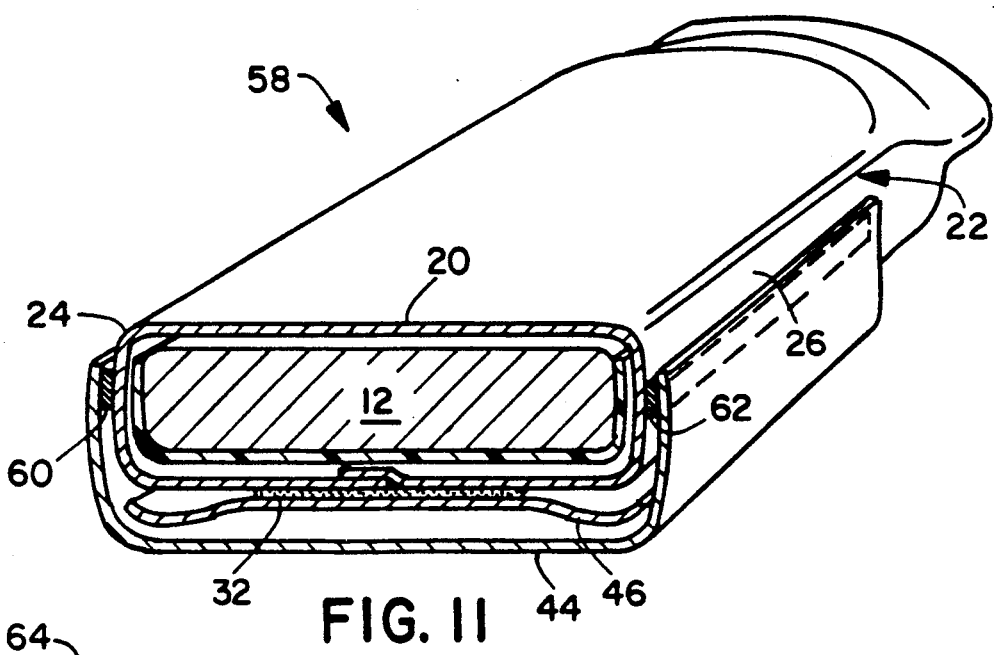
FIG. 11 is a perspective view of an absorbent article and undergarment wherein the protective sheet is attached to the longitudinal side edges of the pad.

Referring to FIG. 11, an absorbent article 58 is shown which is similar to the absorbent article 10 except that a pair of adhesive strips 60 and 62 are secured to the longitudinal side edges 24 and 26 of the pad 22. By placing the adhesive strips 60 and 62 on the sides of the pad 22, it may be easier for the wearer to attach the protective sheet 44. The side attachment also may reduce the overall thickness of the product and facilitates removal of the peel strips without the fear of having the undergarment sticking to all three adhesives strips 32, 36 and 38.

Figure 12:
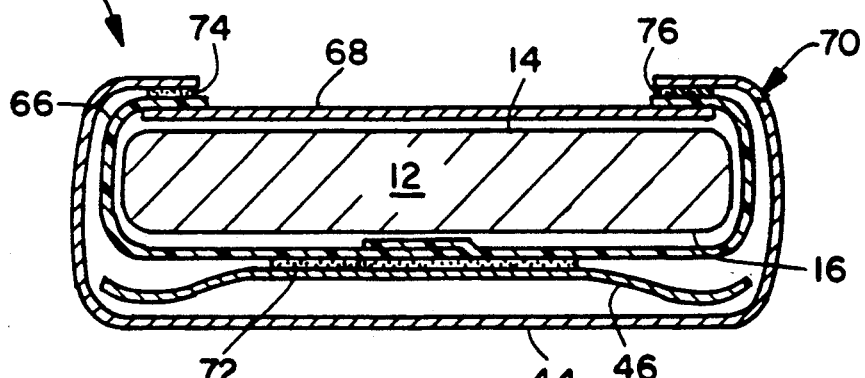
FIG. 12 is a cross-sectional view of an absorbent article enclosed by a baffle and a cover and having a pair of adhesive strips secured to an upper surface of the baffle which provide attachment means for a protective sheet.

Referring to FIG. 12, another embodiment is depicted wherein an absorbent article 64 is shown having the absorbent 12 enclosed by a liquid-impermeable baffle 66 and a liquid-permeable cover 68. The baffle 66 is positioned adjacent to the garment facing surface 16 of the absorbent 12 and extends upward around the sides and wraps over onto the bodyside surface 14 of the absorbent. The absorbent 12, the baffle 66 and the cover 68 form a pad 70 having a garment adhesive strip 72 secured to the baffle 66 along the longitudinal axis of the garment facing surface of the pad 70. A pair of adhesive strips 74 and 76 are secured to the baffle 66 on the bodyside surface of the absorbent article 64. In other words, each of the pair of adhesive strips 74 and 76 are positioned on an opposite side of the garment adhesive strip 72 but each is also aligned on the opposite surface of the absorbent 12. It should be noted that the protective sheet 44 may have to be made a little wider in this embodiment in order to fully wrap around the absorbent article 64 as well as the undergarment 46. This embodiment will provide excellent protection against side leakage of body fluids.

Figure 13:
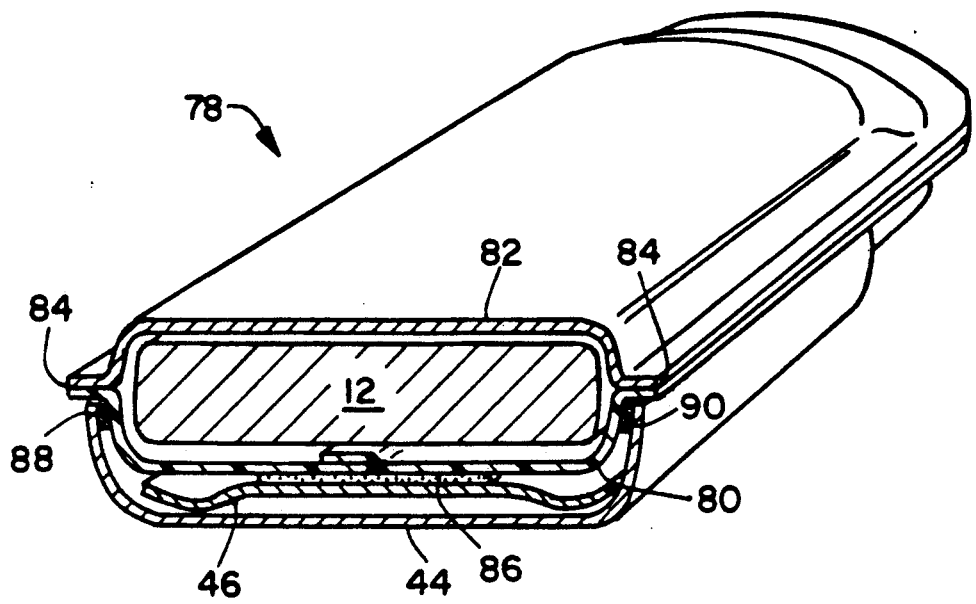
FIG. 13 is a perspective view of another embodiment of an absorbent article showing a liquid-permeable cover and a liquid-impermeable baffle cooperating to enclose an absorbent and having a pair of adhesive strips attached to a lower surface of said baffle which provide attachment means for a protective sheet.

Referring to FIGS. 13, an alternative embodiment is shown wherein an absorbent article 78 contains the absorbent 12 enclosed by a liquid-impermeable baffle 80 and a liquid-permeable cover 82. The baffle 80 and the cover 82 are joined together at their periphery to form a seal 84 at a location approximately half way up the height of the absorbent 12. A garment adhesive strip 86 is secured to the garment facing surface of the baffle 80 and is positioned along the longitudinal axis thereof. A pair of adhesive strips 88 and 90 are secured to the baffle 80 on opposite sides of the garment adhesive strip 84. The pair of adhesive strips 88 and 90 are positioned adjacent to and just below the peripheral seal 84. The pair of adhesive strips provide a means for attaching the protective sheet 44 to the absorbent article 78. By placing the pair of adhesive strips 88 and 90 below the seal 84, the strips 88 and 90 can be sheltered and offset from the outer periphery of the product. This will be advantageous when the protective sheet 44 is not attached because it will mean that the peel strips which cover the pair of adhesive strips 88 and 90 (not shown) will not contact the user's inner thighs and cause irritation or discomfort.

Figure 14:
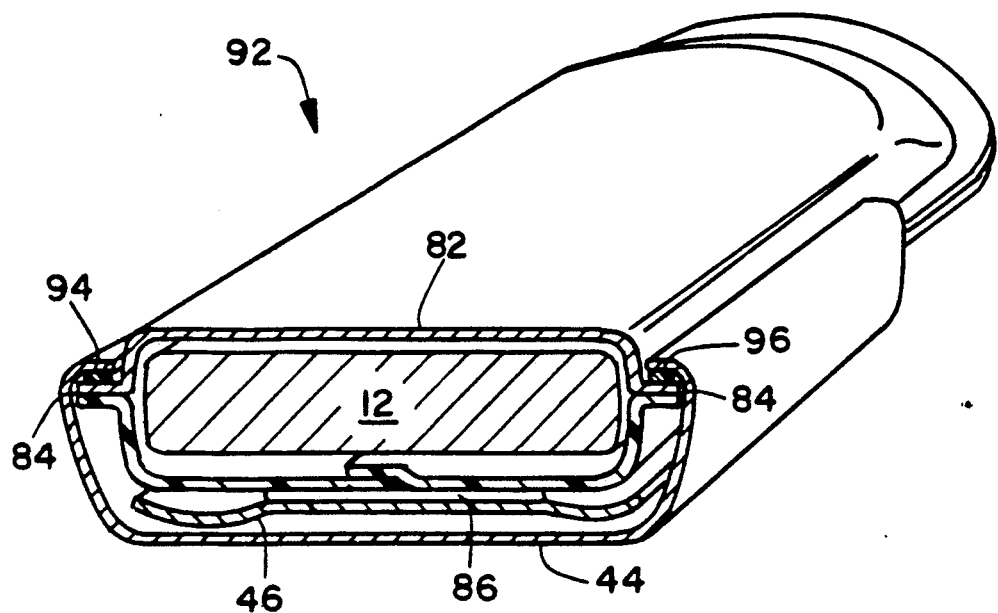
FIG. 14 is a perspective view of another embodiment of an absorbent article showing a liquid-permeable cover and a liquid-impermeable baffle cooperating to enclose an absorbent and having a pair of adhesive strips attached to an upper surface of the cover which provide attachment means for a protective sheet.

Referring to FIG. 14, an alternative embodiment to FIG. 13 is shown wherein an absorbent article 92 is depicted. The absorbent article 92 is similar to absorbent article 78 except that it has a pair of adhesive strips 94 and 96 secured to the cover 82 adjacent to and just above the peripheral seal 84. This design allows the protective sheet 44 to wrap around the seal 84 and provide a smooth outer surface which contacts the inner thighs of the wearer.

Figure 15:
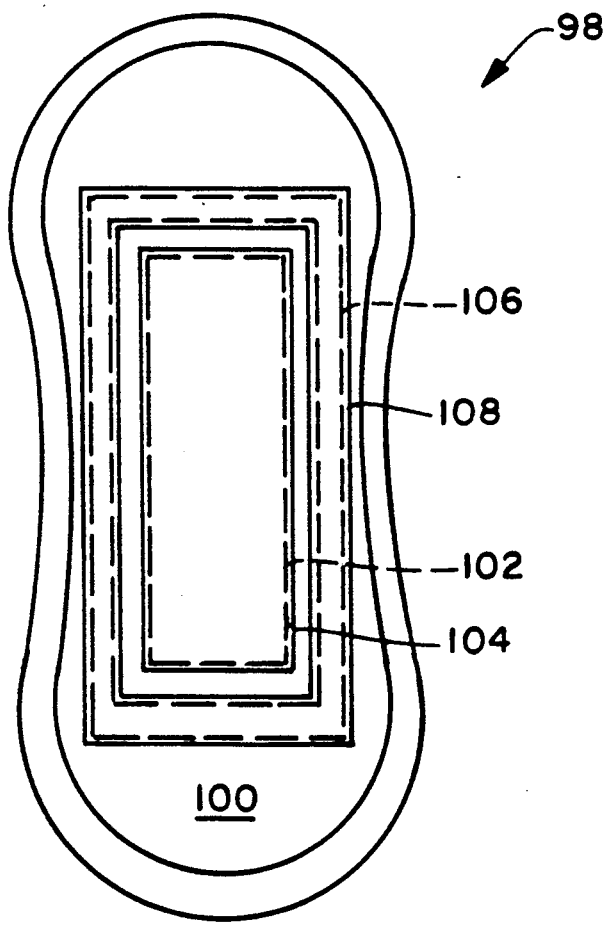
FIG. 15 is a bottom view of an absorbent article showing a garment adhesive strip surrounded by a rectangularly shaped adhesive strip which provides attachment means for a protective sheet.

Lastly, referring to FIG. 15, a bottom view of an absorbent article 98 is shown. The absorbent article 98 contains an absorbent and a liquid-impermeable baffle both of which are enclosed by a liquid-permeable cover 100. The absorbent article 98 has an hourglass shape but could be rectangular if desired. A garment adhesive strip 102 is secured to the garment facing surface of the cover 100 and is covered by a removable peel strip 104. A rectangularly shaped adhesive member 106 is secured to the cover 100 on the garment facing surface and is positioned about the outer periphery of the garment adhesive strip 102. A rectangular peel strip 108 is removably attached to the rectangularly shaped adhesive member 106 and is designed to be removed prior to the attachment of the protective sheet 44. This embodiment could also be modified in that a single peel strip can be used to cover both the garment adhesive 102 and the rectangularly shaped adhesive member 106. This would eliminate the number of individual peel strips which would have to be removed by the wearer. If the wearer decided not to use the protective sheet 44 than both the garment adhesive strip 102 and the rectangularly shaped adhesive member 106 could be used to fasten the absorbent article 98 to the inner surface of the undergarment.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

We claim:

1. An absorbent article designed to be attached to the crotch portion of an undergarment for absorbing human exudate, said article comprising:
   a) an absorbent having a bodyside surface and an opposite garment facing surface;
   b) a liquid-impermeable baffle positioned adjacent to at least said garment facing surface of said absorbent;
   c) a liquid-permeable cover positioned adjacent to at least said bodyside surface of said absorbent and cooperating with said baffle to enclose said absorbent and form a pad, said pad having an external garment facing surface, a pair of longitudinal side edges and a pair of distally spaced ends;
   d) a garment adhesive strip secured to said external garment facing surface of said pad and positioned along the longitudinal axis thereof, said garment adhesive strip providing attachment of said pad to said undergarment;
   e) a pair of adhesive strips secured to said pad and positioned on opposite sides of said garment adhesive strip; and
   f) a protective sheet attachable to said pair of adhesive strips, said sheet having a length approximately equal to the length of one of said pair of adhesive strips and having a width corresponding to about twice the width of the crotch portion of said undergarment, said sheet preventing side leakage of body fluid off of said pad from staining the crotch portion of said undergarment.

2. The absorbent article of claim 1 wherein said cover completely surrounds both said absorbent and said baffle and said garment adhesive strip and said pair of adhesive strips are secured to said cover and face the crotch portion of said undergarment.

3. The absorbent article of claim 1 wherein said cover completely surrounds both said absorbent and said baffle and said pair of adhesive strips are secured to said cover along the longitudinal side edges of said pad.

4. The absorbent article of claim 1 wherein said pair of adhesive strips are secured to said baffle.

5. The absorbent article of claim 1 wherein said protective sheet is liquid-impermeable.

6. The absorbent article of claim 5 wherein said protective sheet is a laminate having at least two layers, one layer being liquid-impermeable and the other layer having a cloth-like texture.

7. The absorbent article of claim 5 wherein said protective sheet is a laminate having three layers with the middle layer being liquid-impermeable and at least one of the other two layers having a cloth-like texture.

8. An absorbent article designed to be attached to the crotch portion of an undergarment for absorbing human exudate, said article comprising:
 a) an absorbent having a bodyside surface and an opposite garment facing surface;
 b) a liquid-impermeable baffle positioned adjacent to at least said garment facing surface of said absorbent;
 c) a liquid-permeable cover completely surrounding both said absorbent and said baffle to form a pad, said pad having an external surface, a pair of longitudinal side edges and a pair of distally spaced ends;
 d) a garment adhesive strip secured to said external surface and positioned along the longitudinal axis of said pad, said garment adhesive strip providing attachment of said pad to said undergarment;
 e) a pair of adhesive strips secured to said cover and positioned on opposite sides of said garment adhesive strip; and
 f) a liquid-impermeable protective sheet attachable to said pair of adhesive strips, said sheet having a length approximately equal to the length of one of said adhesive strips and having a width corresponding to at least twice the width of the crotch portion of said undergarment, said sheet preventing side leakage of body fluid off of said pad from staining the crotch portion of said undergarment.

9. The absorbent article of claim 8 wherein said pair of adhesive strips are positioned on said bodyside surface of said pad.

10. The absorbent article of claim 8 wherein said pair of adhesive strips are secured to said longitudinal side edges of said pad and each has a length approximately equal to the length of said garment adhesive strip.

11. The absorbent article of claim 8 wherein said protective sheet is a laminate having at least one liquid-impermeable layer.

12. The absorbent article of claim 11 wherein said laminate has two layers, one layer being liquid-impermeable and the other layer having a cloth-like texture.

13. The absorbent article of claim 8 wherein peel strips are releasably secured to said garment adhesive strip and to said pair of adhesive strips.

14. An absorbent article designed to be attached to the crotch portion of an undergarment for absorbing human exudate, said article comprising:
 a) an absorbent having a bodyside surface and an opposite garment facing surface;
 b) a liquid-impermeable baffle positioned adjacent to said garment facing surface of said absorbent;
 c) a liquid-permeable cover completely surrounding both said absorbent and said baffle to form a pad, said pad having an external surface, a pair of longitudinal side edges and a pair of distally spaced ends;
 d) a garment adhesive strip secured to said external surface and positioned along the longitudinal axis of said pad, said garment adhesive strip facing said undergarment and providing attachment of said pad to said undergarment;
 e) a pair of adhesive strips secured to said longitudinal side edges of said pad; and
 f) a liquid-impermeable protective sheet attachable to said pair of adhesive strips, said sheet having a length approximately equal to the length of one of said pair of adhesive strips and having a width corresponding to about twice the width of the crotch portion of said undergarment, said sheet preventing side leakage of body fluid off of said pad from staining the crotch portion of said undergarment.

15. The absorbent article of claim 14 wherein said pair of adhesive strips each has a length approximately equal to the length of said garment adhesive strip.

16. The absorbent article of claim 14 wherein said protective sheet is a laminate having at least two layers, one of said layers being liquid-impermeable and the other layer having a cloth-like texture.

17. The absorbent article of claim 14 wherein peel strips are releasably secured to said garment adhesive strip and to said pair of adhesive strips.

18. An absorbent article designed to be attached to the crotch portion of an undergarment for absorbing human exudate, said article comprising:
 a) an absorbent having a bodyside surface and an opposite garment facing surface;
 b) a liquid-impermeable baffle positioned adjacent to at least said garment facing surface of said absorbent;
 c) a liquid-permeable cover positioned adjacent to at least said bodyside surface of said absorbent and cooperating with said baffle to enclose said absorbent and form a pad, said pad having an external garment facing surface, a pair of longitudinal side edges and a pair of distally spaced ends;
 e) a garment adhesive strip secured to said external garment facing surface of said pad and positioned along the longitudinal axis thereof, said garment adhesive strip providing attachment of said pad to said undergarment;
 f) a rectangularly shaped adhesive strip secured to said pad and positioned about the periphery of said garment adhesive strip; and
 g) a protective sheet attachable to said rectangularly shaped adhesive strip, said sheet having a length approximately equal to the length of said rectangularly shaped adhesive strip and having a width corresponding to about twice the width of the crotch portion of said undergarment, said sheet preventing side leakage of body fluid off of said pad from staining the crotch portion of said undergarment.

* * * * *